United States Patent
Wang et al.

(10) Patent No.: US 10,112,962 B2
(45) Date of Patent: Oct. 30, 2018

(54) BORON-BASED PRODRUG STRATEGY FOR INCREASED BIOAVAILABILITY AND LOWER-DOSAGE REQUIREMENTS FOR DRUG MOLECULES CONTAINING AT LEAST ONE PHENOL (OR AROMATIC HYDROXYL) GROUP

(71) Applicant: XAVIER UNIVERSITY OF LOUISIANA, New Orleans, LA (US)

(72) Inventors: Guangdi Wang, New Orleans, LA (US); Qiu Zhong, Metairie, LA (US); Shilong Zheng, New Orleans, LA (US)

(73) Assignee: XAVIER UNIVERSITY, New Orleans, LA (US)

( * ) Notice: Subject to any disclaimer, the term of this patent is extended or adjusted under 35 U.S.C. 154(b) by 0 days.

(21) Appl. No.: 15/323,226

(22) PCT Filed: Jul. 1, 2015

(86) PCT No.: PCT/US2015/038768
§ 371 (c)(1),
(2) Date: Dec. 30, 2016

(87) PCT Pub. No.: WO2016/004166
PCT Pub. Date: Jan. 7, 2016

(65) Prior Publication Data
US 2017/0137443 A1 May 18, 2017

Related U.S. Application Data

(60) Provisional application No. 62/020,101, filed on Jul. 2, 2014.

(51) Int. Cl.
| C07J 31/00 | (2006.01) |
| C07F 5/02 | (2006.01) |
| C07F 5/04 | (2006.01) |
| C07J 51/00 | (2006.01) |
| C07H 23/00 | (2006.01) |

(52) U.S. Cl.
CPC .............. *C07F 5/025* (2013.01); *C07F 5/027* (2013.01); *C07F 5/04* (2013.01); *C07H 23/00* (2013.01); *C07J 31/006* (2013.01); *C07J 51/00* (2013.01)

(58) Field of Classification Search
CPC .................................................... C07J 31/006
See application file for complete search history.

(56) References Cited

U.S. PATENT DOCUMENTS

2005/0239832 A1 10/2005 John et al.
2014/0051661 A1 2/2014 Das et al.

FOREIGN PATENT DOCUMENTS

| WO | 2012/138648 A1 | 10/2012 |
| WO | 2012/151562 A1 | 11/2012 |
| WO | 2013/173488 A1 | 11/2013 |

OTHER PUBLICATIONS

Chemical Abstracts Registry No. 101251-09-6, indexed in the Registry file on STN CAS Online on Apr. 5, 1986.*
Chemical Abstracts Registry No. 214360-60-8, indexed in the Registry file on STN CAS Online on Nov. 17, 1998.*
International Search Report of International Patent Application PCT/US2015/038768 dated Sep. 14, 2015.
Beenen, Melissa A. et al., "Asymmetric Copper-Catalyzed Synthesis of α-Amino Boronate Esters from N-tert-Butanesulfinyl Aldimines", Journal of American Chemical Society, vol. 130, pp. 6910-6911, May 8, 2008.
Das, Bhaskar C. et al., "Design and synthesis of novel pinacolylboronate containing combretastatin 'antimitotic agent' analogues", Tetrahedron Letters, vol. 50, pp. 3031-3034, Apr. 1, 2009.
Jiang, Quan et al., "Boron-Based 4-Hydroxytamoxifen Bioisosteres for Treatment of de Novo Tamoxifen Resistant Breast Cancer", ACS Medicinal Chemistry Letters, vol. 3, pp. 392-396, Apr. 6, 2012.
Das, Bhaskar C. et al., "Design, synthesis and biological study of pinacolyl boronate-substituted stilbenes as novel lipogenic inhibitors", Bioorganic & Medicinal Chemistry Letters, vol. 21, pp. 5638-5641, May 31, 2011.
Liu, Jiawang et al., "Fulvestrant-3 Boronic Acid (ZB716): An Orally Bioavailable Selective Estrogen Receptor Downregulator (SERD)", Journal of Medical Chemistry, Aug. 16, 2016, pp. 8134-8140, vol. 59, ACS Publications.
Zhang, Changde et al., "Metabolism, pharmacokinetics, and bioavailability of ZB716, a Steroidal Selective Estrogen Receptor Downregulator (SERD)", Oncotarget, Oct. 10, 2017, pp. 1-16.
Guo, Shanchun et al., "ZB716, a steroidal selective estrogen receptor degrader (SERD) is orally efficacious in blocking tumor growth in mouse xenograft models", Oncotarget, Jan. 8, 2018, pp. 1-14.

* cited by examiner

*Primary Examiner* — Laura L Stockton
(74) *Attorney, Agent, or Firm* — McBee Moore Woodward & Vanik IP, LLC; Susan McBee; Chester Moore

(57) ABSTRACT

Boron-based prodrugs of phenol- or aromatic hydroxyl group-containing therapeutic molecules ("original drugs"), uses thereof, and methods of making the same, are provided for achieving, for example, improved bioavailability, prolonged retention (e.g., in a circulatory system) and, in particular, significantly lowered therapeutically effective dosage in order to reduce adverse effects while maintaining the desired therapeutic effects of the original drugs.

6 Claims, 9 Drawing Sheets

BORON-BASED PRODRUG STRATEGY FOR INCREASED BIOAVAILABILITY AND LOWER-DOSAGE REQUIREMENTS FOR DRUG MOLECULES CONTAINING AT LEAST ONE PHENOL (OR AROMATIC HYDROXYL) GROUP

CROSS-REFERENCE TO RELATED APPLICATIONS

This Non-Provisional Patent Application claims the benefit of U.S. provisional patent application No. 62/020,101, filed 2 Jul. 2014, and international application no. PCT/US2015/038768, filed 1 Jul. 2015.

STATEMENT REGARDING FEDERALLY SPONSORED RESEARCH OR DEVELOPMENT

This Invention was made with U.S. Government support under Contract No. 8G12MD007595 awarded by the National Institutes of Health. The Government has certain rights in this invention.

BACKGROUND

1. Field

The present disclosure relates to boron-based prodrugs, methods for making the same, methods for increased bioavailability and lowered dosage requirements for drug molecules that contain one or more phenol groups, and the synthesis and use of the same. Further, the present disclosure teaches the utilization of said prodrugs as improved medications with lower-dose and longer-lasting efficacy.

Use of the boron-based prodrugs as improved medications can be particularly beneficial in reducing detrimental side effects and unintentional overdose by using significantly lower doses to achieve the same therapeutic effect as the unmodified drug. Furthermore, the prodrugs described herein afford improved pharmacokinetic properties with longer half-life in plasma, making it possible to reduce the frequency of medication.

2. Description of Related Art

Many active drug molecules contain one or more substituted or unsubstituted phenolic groups, or aromatic hydroxyl groups, and are amenable to the described boron-based modification towards desired prodrugs for enhancement in bioavailability and bio-retention and, in particular, significantly lower the therapeutically effective dosage to reduce adverse effects. Any active drug molecule containing one or more hydroxyl groups as described above can be chemically modified to any of the boronic prodrugs using methods taught in the present disclosure.

Fulvestrant

Fulvestrant is a selective estrogen receptor downregulator (SERD) that was approved by FDA in 2003 as treatment for breast cancer following failure on Tamoxifen and/or aromatase inhibitors (AI). Fulvestrant is a pure anti-estrogen with no known agonist effects. Clinically it has been shown to be as effective as anastrozole when used to treat patients who had recurrence or relapse after Tamoxifen or AI treatment. Due to its poor oral bioavailability, the drug is currently administered by intramuscular (IM) injection at the approved dose of 250 mg (Croxtall et al. *Drugs.* 2011; 71(3):363-80). Further pharmacological and pre-clinical studies suggest that a higher dose of 500 mg may be more effective and clinical trials have been conducted to test the benefits of administering fulvestrant at a higher dose (Stevez et al. *Cancer Treat Rev.* 2013; 39(2):136-41). The data highlight the need to improve bioavailability to make fulvestrant a more effective therapeutic regimen for Tamoxifen-resistant breast cancer.

Acetaminophen

Tylenol is one of the most popular over the counter analgesics (pain killer) and antipyretics (fever reducer) in the United States, making up about 35% of the pain killer market in North America (Lee, *NEJM.* 2003; 349:474-485). Americans take over 8 billion pills (tablets or capsules) of Tylenol each year for treatment of pain symptoms and fever. Acetaminophen is also a common active ingredient present in as many as 600 different over the counter drugs according to a statement issued by the pharmaceutical company Johnson and Johnson. For example, Anacin-3, Liquiprin, Panadol, and various cold and flu medicines all contain acetaminophen. Acetaminophen overdose is currently the most frequent cause of acute liver failure in USA, the UK and many other countries (Larson et al. *Hepatology.* 42:1364-1372, 2005). Each year, acetaminophen-associated overdoses account for about 56,000 emergency room visits and 26,000 hospitalizations (Nourjah et al. *Pharmacoepidemiol Drug Saf.* 2006; 15(6):398-405). In 2001, nearly 50% of all acetaminophen exposures reported were unintentional in nature and more than 50% were treated in a healthcare facility. Overall, acetaminophen-associated fatalities represented 16% of the total 1074 fatalities that were reported in TESS in 2001. Approximately 50% of acetaminophen-associated fatalities occurred in individuals who took single-ingredient acetaminophen products which are available as OTC drugs. Beginning in October 2013, in an effort by Tylenol's parent company, Johnson & Johnson, to reduce the number of accidental acetaminophen overdoses that occur each year, bottles of Extra Strength Tylenol would carry a new warning on the caps: "Contains acetaminophen. Always read the label." This latest move by Johnson & Johnson underscores the continued need to reduce acetaminophen overdose and prevent liver failure and loss of life.

Raloxifene

Raloxifene was approved in 2007 by the U.S. Food and Drug Administration for reducing the risk of invasive breast cancer in postmenopausal women with osteoporosis and in postmenopausal women at high risk for invasive breast cancer. Raloxifene is available in 60 mg tablets taken daily. Common adverse effects include hot flashes and leg cramps. Raloxifene may infrequently cause serious blood clots to form in the legs, lungs, or eyes. Other reactions experienced include leg swelling/pain, trouble breathing, chest pain, vision changes. Raloxifene can also cause developmental abnormalities such as birth defects. The relatively high dosage requirement of raloxifen (for example, compared to 20 mg/day for Tamoxifen and 1 mg/day for anastrozole) is due to its poor bioavailability (Kemp et al. *Drug Metab Dispos.* 2002; 30:694-700; Jeong et al. *Drug Metab Dispos.* 2005; 33:785-94).

Irinotecan (SN-38)

Irinotecan is hydrolysed by carboxylesterases into its active metabolite SN-38 (Garcia-Carbonero et al. *Clin Cancer Res.* 2002; 8(3):641-61). Use of boron-SN-38 ensures the desired concentration level of SN-38 without relying on metabolic conversion of irinotecan. Moreover, boron-SN-38 is preferentially enriched in plasma and in tumor loci, thus requiring significantly lower dosage to achieve the same therapeutic effects as treated by irinotecan at several-fold higher dosage. Such lowered dosage requirement in turn will reduce cytotoxicities of the drug to healthy tissues and organs.

Niclosamide

Niclosamide has been shown to inhibit the spread of colon cancer in animal studies. The drug works by blocking the expression of gene called S100A4/metastasin, which can prompt colon cancer metastasis. However, niclosamide has poor water solubility and low oral bioavailability (Navab et al. *J. Lipid Res.* 2009; 50:1538-1547), thereby limiting its clinical development as a cancer treatment regimen.

The solution to this technical problem is provided by the embodiments characterized in the claims.

BRIEF SUMMARY

The present application provides a method to prepare and use boron-based prodrugs of phenol- or aromatic hydroxyl group-containing therapeutic molecules for the purpose of improved bioavailability, prolonged retention in patients' body, especially in the blood circulatory system. Selected examples of such prodrugs have been tested in vivo to have significantly increased plasma concentrations of the active drug forms. Mice given the same oral dose of the boron prodrugs were found to have 5-10 times higher concentrations of the active drug forms than in mice fed with the same dose of the original drugs. Consequently, the boron-based prodrugs address an important need in the art to enhance bioavailability and retention, offer oral bioavailability, and reduce therapeutically effective dosages for a variety of existing small molecule drugs.

In an embodiment, a boron-fulvestrant prodrug offers an oral administration formulation or an IM injection option that has the potential to improve efficacy over existing fulvestrant therapy. In another embodiment, boron-containing paracetamol (acetaminophen) prodrugs have 5-10 fold increases in the plasma concentrations of paracetamol, thus reducing the therapeutically effective dose requirement to a level that is much less likely to cause accidental overdose. In another embodiment, boron-raloxifene prodrug lowers the dosage by 5-10 fold to achieve the same blood concentration of the drug, thereby significantly reducing potential side effects. In another embodiment, a boron-niclosamide prodrug approach enhances oral bioavailability by 5-10 fold as reflected in the elevated blood concentration in mice following oral administration compared to niclosamide.

Thus, in an embodiment, the boron-containing prodrugs of the present disclosure are compounds of the formula (I):

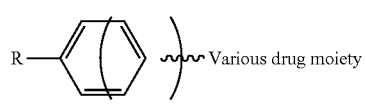

(I)

wherein R is:

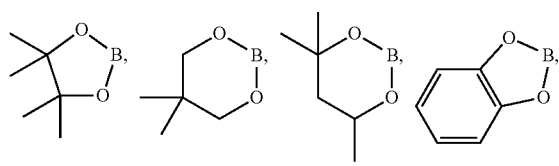

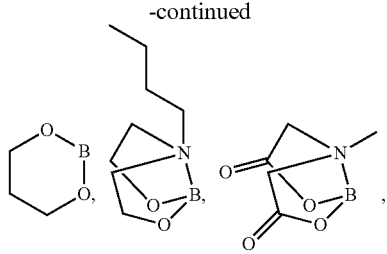

or $KF_3B$, $(HO)_2B$, $NaF_3B$, and wherein the R substituent point of attachment to a substituted or unsubstituted phenolic group or aromatic hydroxyl group of a drug molecule is on R the substituent boron atom, as depicted more fully by the example prodrug structures of Table 1 below.

As used herein, the terms "boron-containing prodrug" and "boron-based prodrug" mean a drug molecule having at least one substituted or unsubstituted phenolic group or aromatic hydroxyl group, wherein the at least one substituted or unsubstituted phenolic group or aromatic hydroxyl group is replaced with an R group. As used herein, the terms "original drug" and "original drug molecule" mean a drug molecule having at least one substituted or unsubstituted phenolic group or aromatic hydroxyl group, wherein the at least one substituted or unsubstituted phenolic group or aromatic hydroxyl group is available to be replaced with an R group.

In a preferred embodiment, the boron-containing prodrugs are compounds having the following structure for R, denoted prodrug 1:

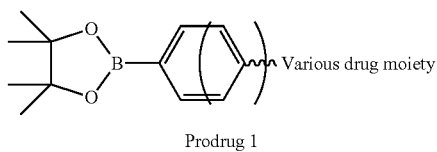

Prodrug 1

For the sake of clarity, the phenyl ring of Prodrug 1 represents a substituted or unsubstituted phenolic group or aromatic hydroxyl group from the original drug, and is a portion of the "various drug moiety" of Prodrug 1. This is shown in greater detail by the examples of Table 1.

In an embodiment, the disclosure provides for a pharmaceutical composition in the form of at least one boron-containing prodrug for treatment of diseases and/or symptoms that are meant to be treated by the original drug molecule (i.e., the prodrug molecule with an —OH moiety in place of the prodrug R moiety). The composition may comprise at least one boron-based prodrug in an amount that is as therapeutically effective as or more therapeutically effective than the original drug.

The disclosure therefore relates to use of a boron-based prodrug according to Formula I for treatment of diseases and/or symptoms that are meant to be treated by the original drug molecule.

The pharmaceutical compositions of the present disclosure can be in any form known to those of skill in the art. For instance, in some embodiments the pharmaceutical compositions are in a form of a product for oral delivery, said product form being selected from a group consisting of a concentrate, dried powder, liquid, capsule, pellet, and pill. In other embodiments, the pharmaceutical compositions of the disclosure are in the form of a product for parenteral administration including intravenous, intradermal, intramuscular, and subcutaneous administration. The pharmaceutical compositions disclosed herein may also further comprise carriers, binders, diluents, and excipients.

Also, in other aspects, the present disclosure relates to new boron-based prodrug compounds and their pharmaceutically acceptable salts; pharmaceutical compositions comprising the new boron-based prodrug compounds, either alone or in combination with at least one additional therapeutic agent, with a pharmaceutically acceptable carrier; and uses of the new boron-based prodrug compounds, either alone or in combination with at least one additional therapeutic agent, in the treatment of diseases and/or symptoms meant to be treated by the original drugs. The combination with an additional therapeutic agent may take the form of combining the new boron-based prodrug compounds with any known therapeutic agent.

Moreover, the presently taught boron-based prodrug platform allows facile oxidative cleavage of the boron-aryl carbon bond to yield aryl-hydroxyl structure of the desired active drug form in the blood of mice, after orally administered to the mice. Thus, the presently disclosed prodrugs can be useful in treating any symptoms that are currently treated by the various drugs described herein, but at a significantly lower dosage, thereby making it unlikely to have any accidental overdose. The methods taught herein may relate to administering the disclosed prodrugs to a patient in need thereof.

It is a further object of the disclosure to provide boronic prodrug compounds, methods of synthesizing the prodrug compounds, methods of manufacturing the prodrug compounds, and methods of using the prodrug compounds.

Another object of the disclosure is to provide a composition, for example a pharmaceutical composition, comprising at least one boron-based prodrug in an amount effective for an indication intended for the original drug, including but not limited to reducing pain and fever, minimizing cold symptoms, alleviating arthritis-induced discomfort, pain, or inflammation.

A further object of the disclosure is a kit, comprising a composition containing at least one boron-based prodrug for treatment of the indication(s) intended for the original drug. The composition of the kit may comprise at least one carrier, at least one binder, at least one diluent, at least one excipient, at least one other therapeutic agent, or mixtures thereof.

The methods for treating a clinical indication by the boron-based prodrug compounds disclosed herein, may be effectuated by administering a therapeutically effective amount of the prodrug to a patient in need thereof, this therapeutically effective amount may comprise administration of the prodrug to the patient at 1 mg/kg/day, 2 mg/kg/day, 3 mg/kg/day, 4 mg/kg/day, 5 mg/kg/day, 10 mg/kg/day and 20 mg/kg/day. Alternatively, amounts ranging from about 0.001 mg/kg/day to about 0.01 mg/kg/day, or about 0.01 mg/kg/day to about 0.1 mg/kg/day, or about 0.1 mg/kg/day to about 1 mg/kg/day, or about 1 mg/kg/day to 10 mg/kg/day, or about 10 mg/kg/day to about 100 mg/kg/day are also contemplated.

In certain aspects, the at least one boron-based prodrug analog has a purity of ≥75%, ≥80%, ≥85%, ≥90%, ≥95%, ≥96%, ≥97%, or ≥98%, and preferably ≥99%.

While certain features of this invention shown and described below are pointed out in the annexed claims, the invention is not intended to be limited to the details specified, since a person of ordinary skill in the relevant art will understand that various omissions, modifications, substitutions, and changes in the forms and details of the invention illustrated and in its operation may be made without departing in any way from the spirit of the present invention. No feature of the invention is critical or essential unless it is expressly stated as being "critical" or "essential."

These and other features, aspects, and advantages of embodiments of the present disclosure will become better understood with regard to the following description, claims, and accompanying drawings explained below.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Figure 1:
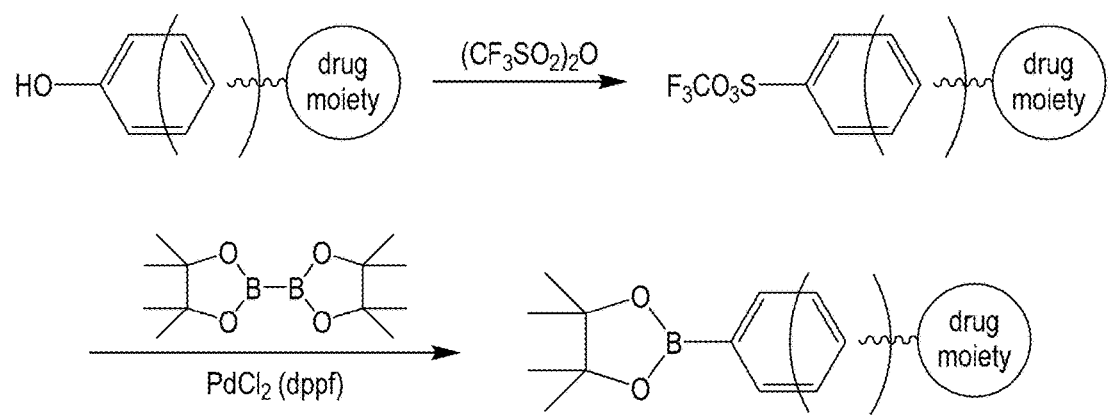
FIG. 1 shows the general synthetic scheme for preparation of boron-based prodrugs from various drug molecules containing at least one aromatic hydroxyl group.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

The subject disclosure features, in one aspect, the synthesis of boron-based prodrugs of various existing therapeutic drug molecules by modifying the phenolic structure in them. To determine whether these prodrugs have enhanced bioavailability in vivo, pharmacokinetic studies were performed in which selected boron-prodrugs were orally administered to mice as a single dose at 5 mg/kg and the drug concentrations in mouse blood were monitored over a period of 24 hours.

As used herein, the term "minimize" or "reduce", or derivatives thereof, include a complete or partial inhibition of a specified biological effect (which is apparent from the context in which the terms "minimize" or "reduce" are used).

Examples of existing original drugs that can utilize the boron-prodrug platform where R is

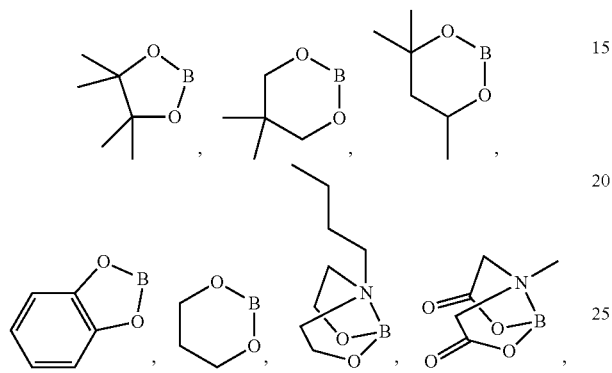

or $KF_3B$, $(HO)_2B$, $NaF_3B$, wherein the R substituent point of attachment is on the boron atom, are provided by Formulas 1 through 57 of Table 1, along with the corresponding original drugs.

TABLE 1

| Original Drug Molecule | Molecular Structure of Original Drug | Examples of Pinacolyl Boronate Ester-prodrug Structure |
|---|---|---|
| Aceta-minophen | (structure of acetaminophen with OH) | (structure with R) (1) |
| Acolbifene | (structure of acolbifene with OH groups) | (structure with R groups) (2) |
| Amo-diaquine | (structure of amodiaquine with OH) | (structure with R) (3) |

TABLE 1-continued

| Original Drug Molecule | Molecular Structure of Original Drug | Examples of Pinacolyl Boronate Ester-prodrug Structure |
|---|---|---|
| Amoxicillin | (structure) | (4) |
| Amrubicin | (structure) | (5) |
| Apomorphine | (structure) | (6) |

TABLE 1-continued
| Original Drug Molecule | Molecular Structure of Original Drug | Examples of Pinacolyl Boronate Ester-prodrug Structure |
|---|---|---|
| Arzoxifene | 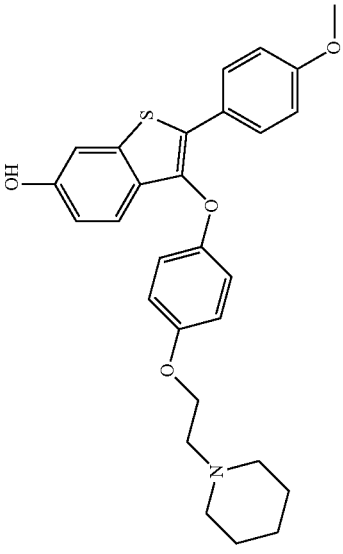 | 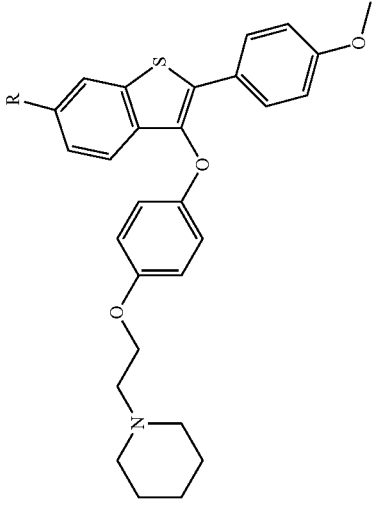 (7) |
| Bazedoxifene | 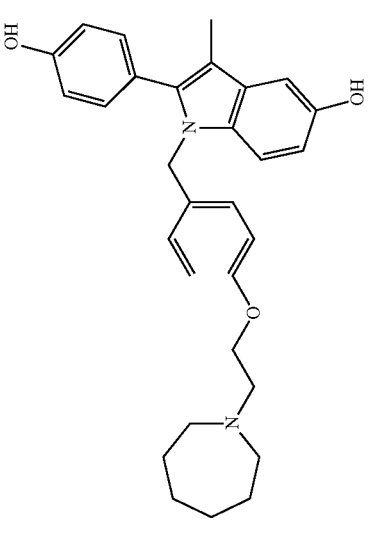 | 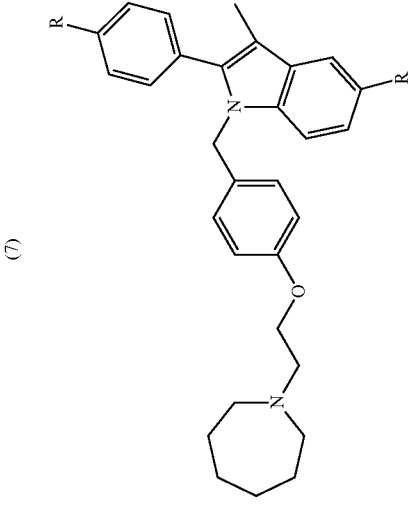 (8) |

TABLE 1-continued

| Original Drug Molecule | Molecular Structure of Original Drug | Examples of Pinacolyl Boronate Ester-prodrug Structure |
|---|---|---|
| Buprenorphine | | (9) |
| Carbidopa | | (10) |
| Cefadroxil | | (11) |

TABLE 1-continued

| Original Drug Molecule | Molecular Structure of Original Drug | Examples of Pinacolyl Boronate Ester-prodrug Structure |
|---|---|---|
| Cefoperazone | [chemical structure] | [chemical structure] (12) |
| Cefprozil | [chemical structure] | [chemical structure] (13) |

TABLE 1-continued

| Original Drug Molecule | Molecular Structure of Original Drug | Examples of Pinacolyl Boronate Ester-prodrug Structure |
|---|---|---|
| Curcumin | (chemical structure) | (14) |
| Daidzein | (chemical structure) | (15) |
| Danorubicin | (chemical structure) | (16) |

TABLE 1-continued
| Original Drug Molecule | Molecular Structure of Original Drug | Examples of Pinacolyl Boronate Ester-prodrug Structure |
|---|---|---|
| Demeclocycline | 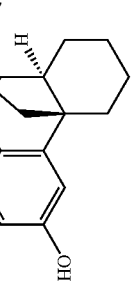 | 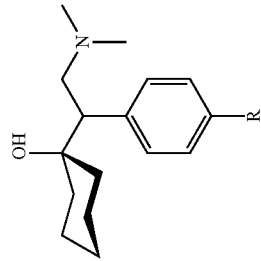 |
| Desvenlafaxine | 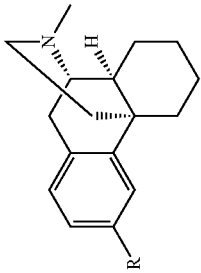 | 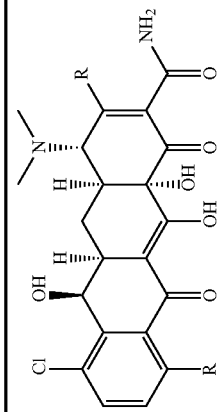 (17) |
| Dextrophan (DXO) | | 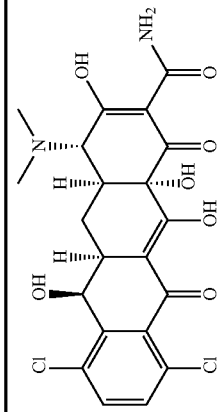 (18) (19) |

TABLE 1-continued
| Original Drug Molecule | Molecular Structure of Original Drug | Examples of Pinacolyl Boronate Ester-prodrug Structure |
|---|---|---|
| Dolutegravir | 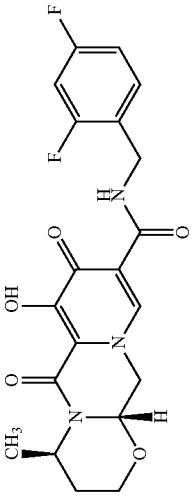 | 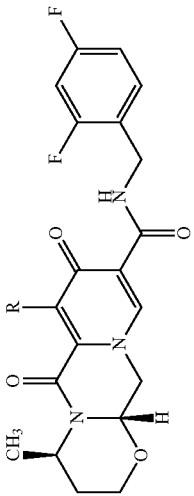 (20) |
| Doxorubicin | 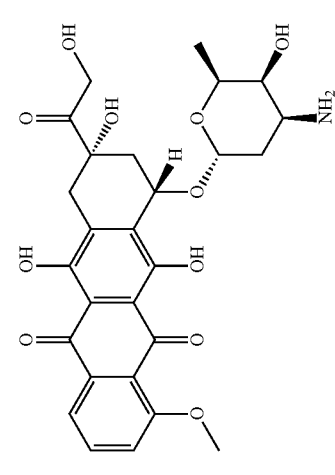 | 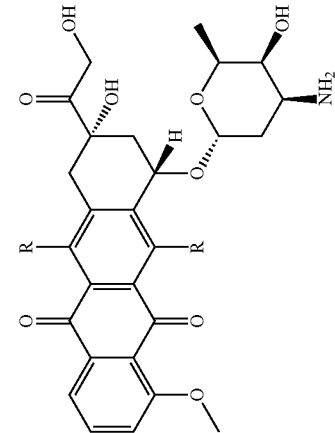 |
| Doxycycline | 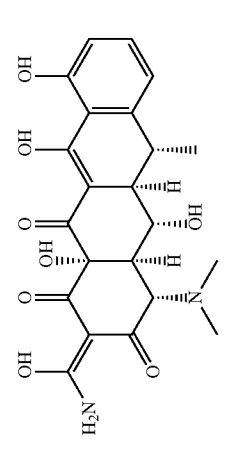 | 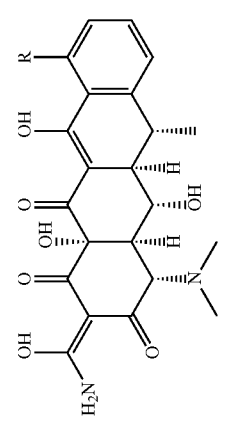 (21) (22) |

TABLE 1-continued

| Original Drug Molecule | Molecular Structure of Original Drug | Examples of Pinacolyl Boronate Ester-prodrug Structure |
|---|---|---|
| Droloxifene | (structure with OH) | (23) |
| Equol | (structure with two OH) | (24) |
| Fenretinide | (structure with OH) | (25) |

TABLE 1-continued

| Original Drug Molecule | Molecular Structure of Original Drug | Examples of Pinacolyl Boronate Ester-prodrug Structure |
|---|---|---|
| Fidaxomicin | (structure of fidaxomicin) | (structure 26) |
| Formestane | (structure of formestane) | (structure 27) |

TABLE 1-continued
| Original Drug Molecule | Molecular Structure of Original Drug | Examples of Pinacolyl Boronate Ester-prodrug Structure |
|---|---|---|
| Formoterol | 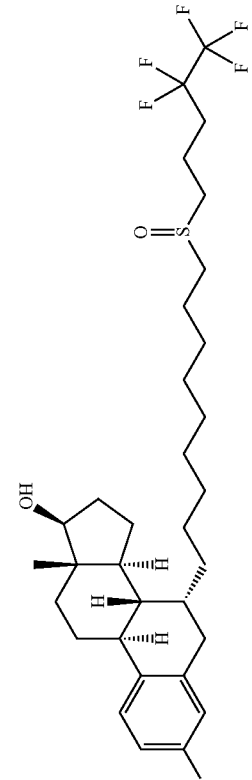 | 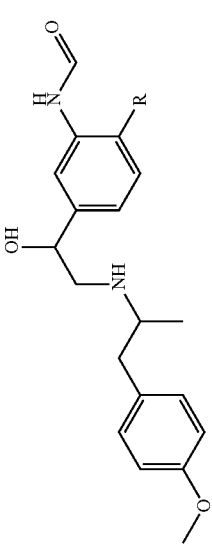 (28) |
| Fulvestrant | 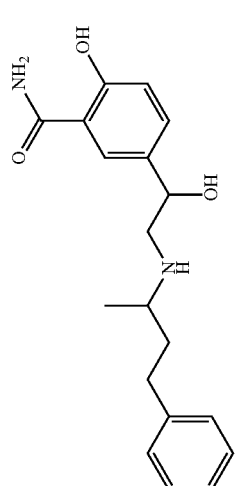 | 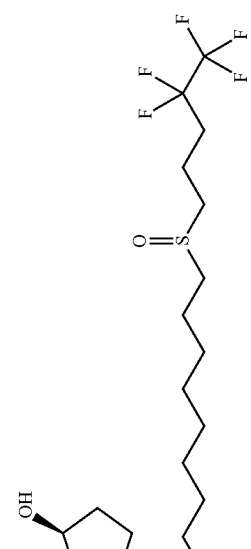 (29) |
| Labetalol | 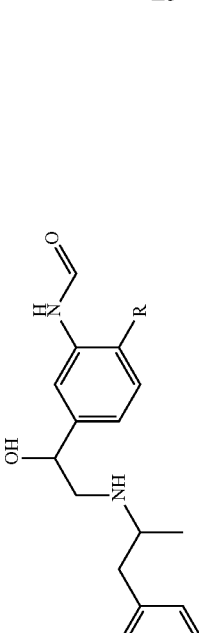 | 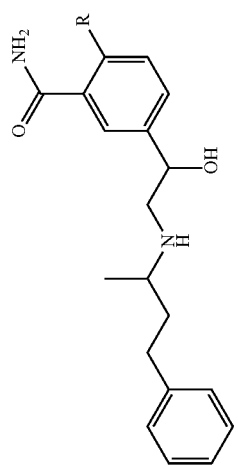 (30) |

TABLE 1-continued

| Original Drug Molecule | Molecular Structure of Original Drug | Examples of Pinacolyl Boronate Ester-prodrug Structure |
|---|---|---|
| Lasofoxifene | (structure) | (31) |
| Levodopa | (structure) | (32) |
| Levoxyl (L-thyroxine) | (structure) | (33) |

TABLE 1-continued

| Original Drug Molecule | Molecular Structure of Original Drug | Examples of Pinacolyl Boronate Ester-prodrug Structure |
|---|---|---|
| Meloxicam | (structure of meloxicam) | (34) |
| Methyldopa | (structure of methyldopa) | (35) |
| Minocycline | (structure of minocycline) | (36) |

TABLE 1-continued

| Original Drug Molecule | Molecular Structure of Original Drug | Examples of Pinacolyl Boronate Ester-prodrug Structure |
|---|---|---|
| Mycophenolic acid | (mycophenolic acid structure with OH) | (37) (mycophenolic acid structure with R) |
| Nelfinavir | (nelfinavir structure with OH) | (38) (nelfinavir structure with R) |
| Niclosamide | (niclosamide structure with OH) | (39) (niclosamide structure with R) |

TABLE 1-continued

| Original Drug Molecule | Molecular Structure of Original Drug | Examples of Pinacolyl Boronate Ester-prodrug Structure |
|---|---|---|
| Nonabine | (structure with OH) | (40) (structure with R) |
| Norepinephrine | (R)-structure with OH, OH, NH₂ | (41) (R)-structure with OH, R, R, NH₂ |
| Oxytetracycline | (structure) | (42) (structure with R) |

TABLE 1-continued

| Original Drug Molecule | Molecular Structure of Original Drug | Examples of Pinacolyl Boronate Ester-prodrug Structure |
|---|---|---|
| Platensimycin | (structure) | (43) |
| Raloxifene | (structure) | (44) |
| Raltegravir | (structure) | (45) |

TABLE 1-continued

| Original Drug Molecule | Molecular Structure of Original Drug | Examples of Pinacolyl Boronate Ester-prodrug Structure |
|---|---|---|
| Resveratrol | (structure of resveratrol) | (46) |
| Rifabutin | (structure of rifabutin) | (47) |

TABLE 1-continued

| Original Drug Molecule | Molecular Structure of Original Drug | Examples of Pinacolyl Boronate Ester-prodrug Structure |
|---|---|---|
| Rifampicin | [chemical structure of rifampicin] | [chemical structure (48) with R groups] |
| Rifapentine | [chemical structure of rifapentine] | [chemical structure (49) with R groups] |

TABLE 1-continued
| Original Drug Molecule | Molecular Structure of Original Drug | Examples of Pinacolyl Boronate Ester-prodrug Structure |
|---|---|---|
| Salbutamol (Albuterol) | 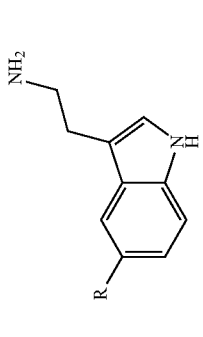 | 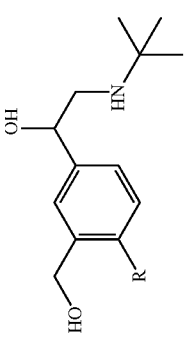 (50) |
| Serotonin | 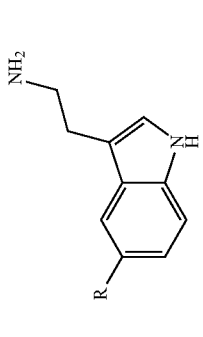 | 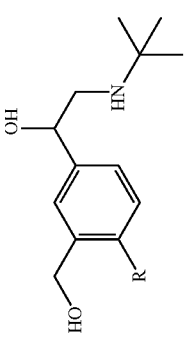 (51) |
| SN-38 | 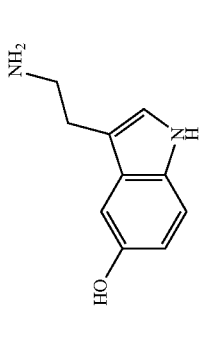 | 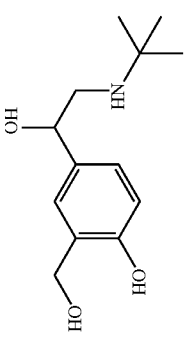 (52) |

TABLE 1-continued

| Original Drug Molecule | Molecular Structure of Original Drug | Examples of Pinacolyl Boronate Ester-prodrug Structure |
|---|---|---|
| Sulfa-salazine | (structure of sulfasalazine) | (53) |
| Tetra-cycline | (structure of tetracycline) | (54) |

TABLE 1-continued

| Original Drug Molecule | Molecular Structure of Original Drug | Examples of Pinacolyl Boronate Ester-prodrug Structure |
|---|---|---|
| Tolterodine (Detrol) | (structure of tolterodine with OH group) | (55) (structure with R group replacing OH) |
| Trabectedin | (structure of trabectedin with HO groups) | (56) (structure with R groups replacing OH) |

TABLE 1-continued

| Original Drug Molecule | Molecular Structure of Original Drug | Examples of Pinacolyl Boronate Ester-prodrug Structure |
|---|---|---|
| Vapreotide (Sanvar) | [structure] | [structure] (57) |

Preferably, R is

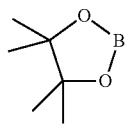

Also provided is the use of at least one compound of Formulas 1 through 57 for treatment of a disease or symptom that is treated or treatable by said compound in which said R is —OH, in a mammal in need thereof.

Also provided is a compound of Formulas 1 through 57 for use as a medicament, for use in the treatment of cancer in a mammal in need thereof, for use in providing analgesia to or reducing inflammation in a mammal in need thereof, for modulating an estrogen receptor, or for use in treating a bacterial, viral, fungal, or *mycoplasma* infection in a mammal in need thereof.

In an embodiment, disease or symptom is selected from the group consisting of: a bacterial, viral, fungal, or *mycoplasma* infection; cancer; ulcer; Parkinson's disease; tuberculosis; leprosy; brucellosis; opioid addiction; arthritis; osteoarthritis; rheumatoid arthritis; leukemia; depression; cough or common cold; human immunodeficiency virus (HIV); anthrax; asthma; bronchitis; hypothyroidism; hypertension; hypotension; congestive heart failure; graft-versus-host disease; helminth infection; *mycobacterium avium* complex (MAC) disease; ulcerative colitis; overactive bladder; urinary incontinence; and esophageal variceal bleeding.

A synthetic procedure for preparation of the boronic derivatives of the various pharmaceutically active compounds containing at least one aromatic hydroxyl group involves reaction of the above compounds with trifluoromethanesulfonic anhydride or 1,1,1-trifluoro-N-phenyl-N-((trifluoromethyl)sulfonyl) methanesulfonamide to form the triflate. This reaction uses the solvent of dimethyl formamide (DMF) in the presence of an organic base such as pyridine. The triflate thus formed is allowed to react with bis(pinacolato)diboron in the presence of a catalyst, $PdCl_2$ (dppf) to form the pinacolyl boronate ester prodrug of the active compound.

For example, boronic derivatives of acetaminophen as prodrug candidates were designed by replacing the hydroxyl group with a boron atom that is linked to various functional groups. A schematic of the synthesis of boron-acetaminophen prodrugs is provided in FIG. 2.

Figure 2:
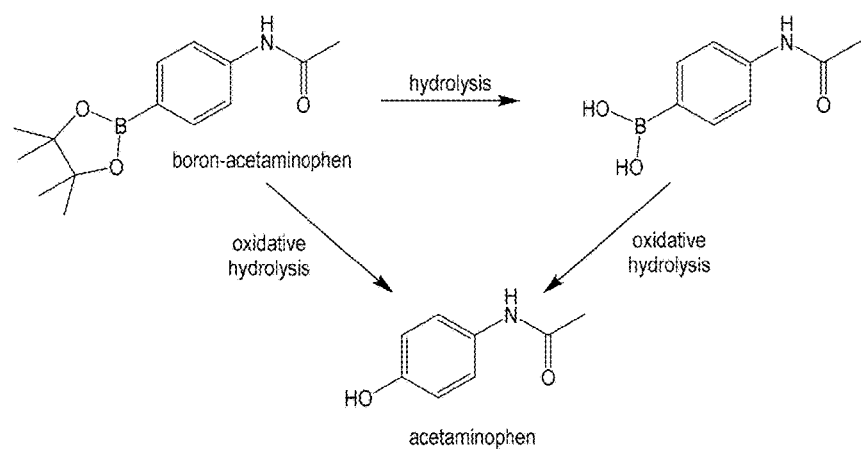
FIG. 2 shows the facile conversion of boron-acetaminophen prodrug to the original drugs under physiological conditions.

The first step of hydrolysis proceeds rapidly in an aqueous environment, while the second step of hydrolysis is known to require physiological conditions such as liver microsome or plasma where oxidative deboronation catalyzed by P450 enzymes leads to rather complete conversion of the boronic prodrug to the original hydroxyl-containing drug molecule, consistent with previous reports on other boronic acid compounds (Pekol et al., *Drug Metab Dispos.* 2005; 33(6):771-7.). As illustrated in FIG. 2, boron-acetaminophen in aqueous solution quickly hydrolyzed to form its boronic acid counterpart, where the ratio of boronate ester to the acid intermediate reached 9:1 within 5 hours. Oxidative deboronation under acidic or basic conditions, or in the presence of oxidizing agents such as $H_2O_2$, leads to the original hydroxyl containing drug molecule.

Boronic derivatives of fulvestrant as prodrug candidates were designed by replacing the hydroxyl group with a boron atom that is linked to various functional groups. A schematic of the synthesis of boron-fulvestrant prodrugs is provided in FIG. 4.

The below Examples will further illustrate the chemical structure of various embodiments of the boron-based prodrug compounds taught herein. Furthermore, the Examples demonstrate the efficacy of various embodiments of the disclosed prodrug compounds. As set forth in the scientific data below, it has been surprisingly found that the disclosed boron-based prodrug compounds exhibit superior bioavailability compared to the parent compounds.

EXAMPLE 1

Figure 3:
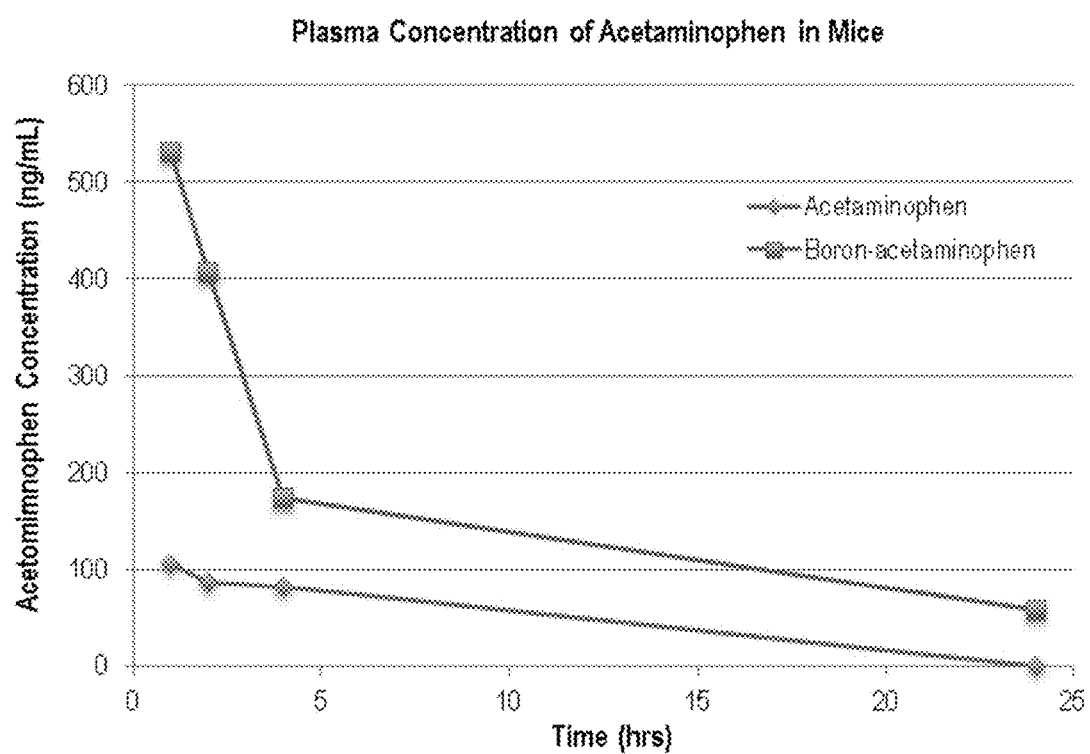
FIG. 3 shows the pharmacokinetics of boron-acetaminophen in mouse plasma.

Pinacolyl Boronate Ester Prodrug of Acetaminophen (FIGS. 2 & 3)

To determine if boron-acetaminophen derivatives have enhanced bioavailability in vivo, pharmacokinetic studies were performed in mice where boron-acetaminophen was orally administered to mice as a single dose at 5 mg/kg and the drug concentrations in mouse blood were monitored over a period of 24 hours.

The boron-containing acetaminophen prodrug showed 5-10 fold increases in the plasma concentrations of acetaminophen, thus reducing the therapeutically effective dose requirement to a level that is much less likely to cause accidental overdose.

The results of these studies are presented in FIG. 3 and demonstrate a significant increase in plasma concentration (bioavailability) of acetaminophen in mice administered boron-acetaminophen compared to mice administered an equal dose of acetaminophen.

EXAMPLE 2

Figure 4:
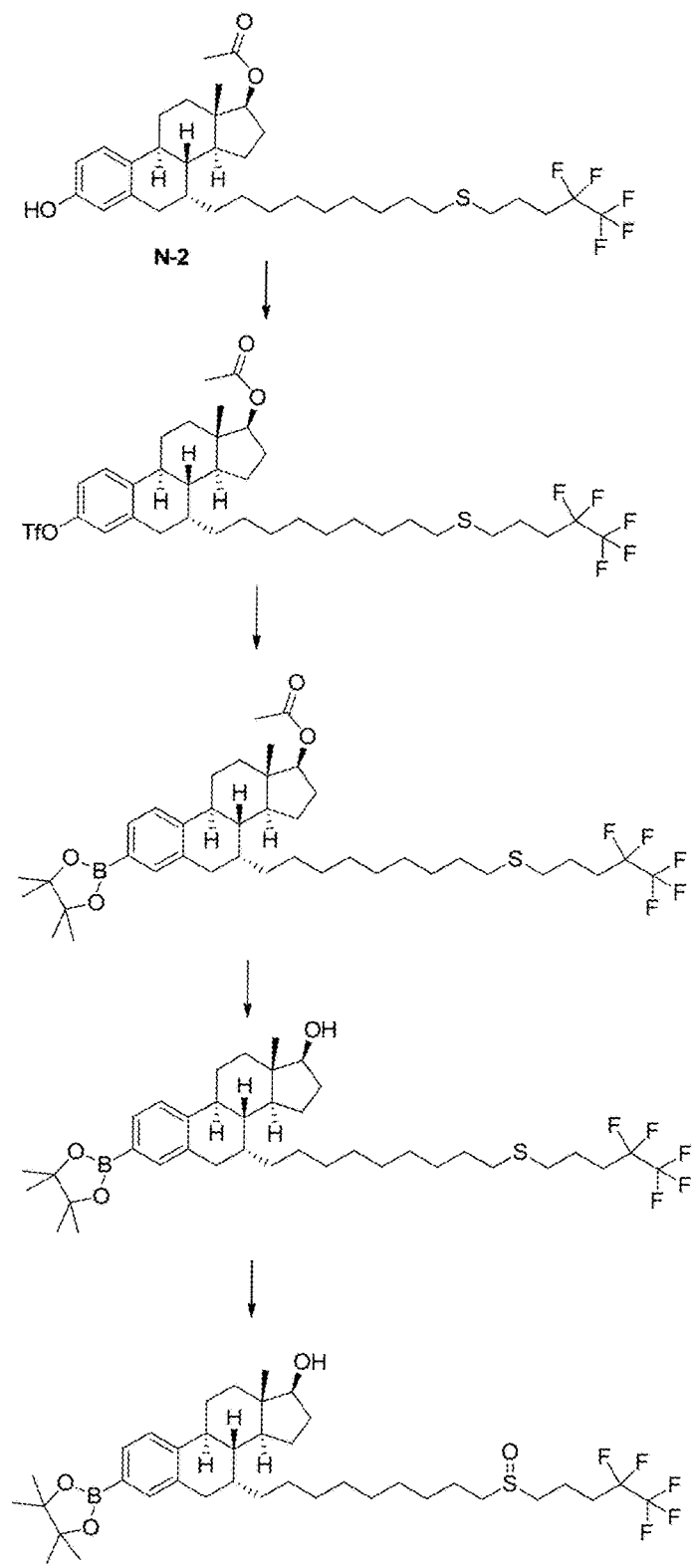
FIG. 4 shows the synthetic scheme for preparation of the pinacolyl boronate ester prodrug of fulvestrant.
Figure 5:
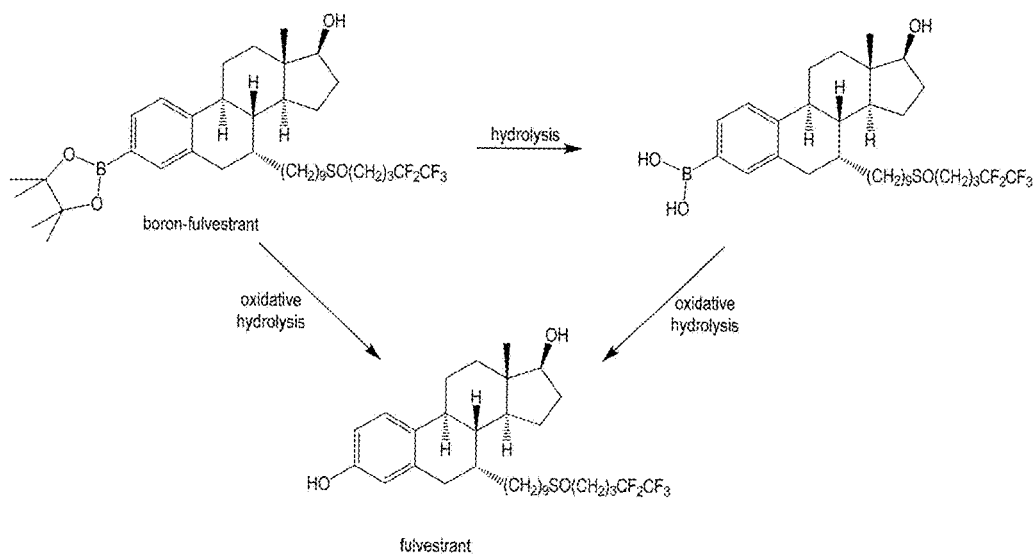
FIG. 5 shows the facile conversion of boron-fulvestrant prodrug to the original drugs under physiological conditions.
Figure 6:
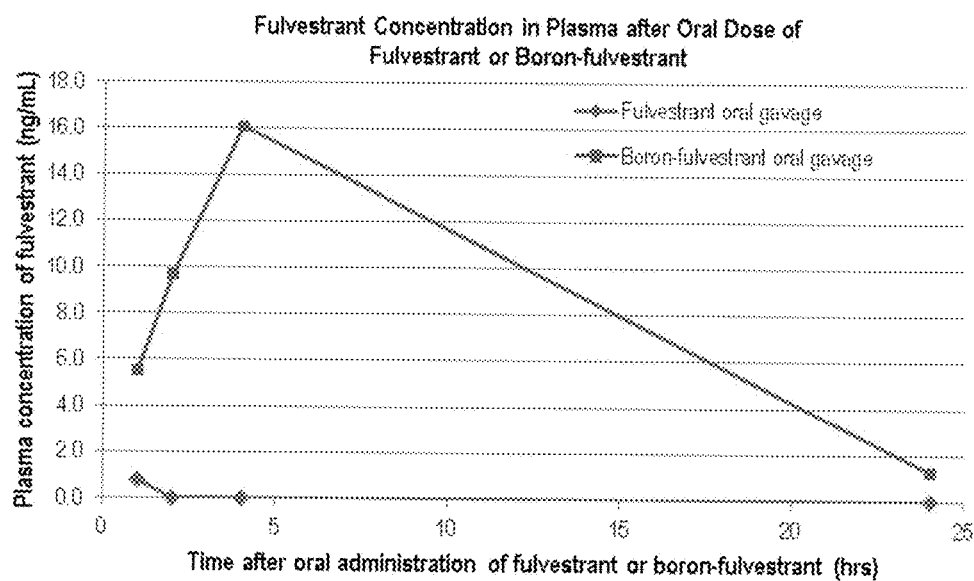
FIG. 6 shows the pharmacokinetics of boron-fulvestrant in mouse plasma.

Pinacolyl Boronate Ester Prodrug of Fulvestrant (FIGS. 4-6)

Step 1: To a solution of N-2 (0.80 g) and pyridine (0.24 mL) in DCM (15 mL) was added trifluoromethanesulfonic acid anhydride (0.2 mL) dropwise at −10° C., and the resulting mixture was stirred until the reaction was finished. The reaction was quenched with satd. sodium carbonate solution and extracted with ethyl acetate. The combined organic layer was dried over $MgSO_4$ and concentrated. The crude was purified by flash column to afford liquid product (0.70 g).

Step 2: The mixture of the triflate of N-2 (0.76 g), bis(pinacolato)diboron (0.378 g), potassium acetate (0.268 g, 9.72 mmol), $Pd(OAc)_2$ (30 mg) and tricyclohexylphosphine (60 mg) in acetonitrile (20 mL) was stirred at 80° C. under $N_2$ overnight. The solvent was removed under vacuum and the crude was purified by flash chromatography to afford product (0.50 g).

Step 3: To a solution of the pinacolyl boronate ester of N-2 (0.5 g) in MeOH-THF (1:1, 4 mL) was added a solution of KOH (0.132 g) in MeOH (2 mL) slowly at 0° C. The resultant mixture was stirred at room temperature for 4 h. After the reaction solution was neutralized with acetic acid, the solvent was removed under vacuum and the crude was purified to afford liquid product (0.40 g).

Step 4: To a solution of the deacetylated pinacolyl boronate ester of N-2 (0.55 g) in DCM (10 mL) was added mCPBA (0.135 g) at 0° C. The resultant mixture was stirred at 0° C. until the starting material was almost transformed to product completely. The reaction solution was diluted with DCM, then washed with saturated $Na_2CO_3$ and dried. The solvent was removed under vacuum and the crude was purified to afford solid product (0.42 g). $^1$H-NMR (CDCl$_3$, 300 MHz): 7.60 (d, J=7.2 Hz, 1H), 7.55 (s, 1H), 7.33 (d, J=7.2 Hz, 1H), 3.76 (m, 1H), 2.89-2.63 (m, 6H), 2.42-2.14 (m, 7H), 1.93 (d, J=12.3 Hz, 1H), 1.80-1.00 (m, 4H), 0.79 (s, 3H). $^{13}$C-NMR (CDCl$_3$, 75 MHz): 143.2, 136.7, 134.9, 132.0, 125.4, 83.6, 82.0, 52.7, 51.0, 46.6, 43.3, 41.7, 38.9, 37.0, 34.3, 33.2, 30.6, 30.0, 29.6, 29.3, 29.2, 28.8, 28.3, 26.9, 25.7, 24.9, 24.8, 22.64, 22.56, 14.6, 11.1. HR-MS (ESI(+)): Calcd for C$_{38}$H$_{59}$BF$_5$O$_4$S (M+H): 717.4147. Found: 717.4160.

To determine if boron-fulvestrant derivatives have enhanced bioavailability in vivo, pharmacokinetic studies were performed in mice where boron-fulvestrant was orally administered to mice as a single dose at 5 mg/kg and the drug concentrations in mouse blood were monitored over a period of 24 hours.

In a period of 24 hours post oral administration of either fulvestrant or boron-fulvestrant, plasma concentration of fulvestrant from orally administered boron-fulvestrant was significantly higher than in mice fed with oral gavage of unmodified fulvestrant.

The results of these studies are presented in FIG. 6 and demonstrate a significant increase in plasma concentration of fulvestrant in mice administered boron-fulvestrant compared to mice administered an equal dose of fulvestrant.

EXAMPLE 3

Figure 7:
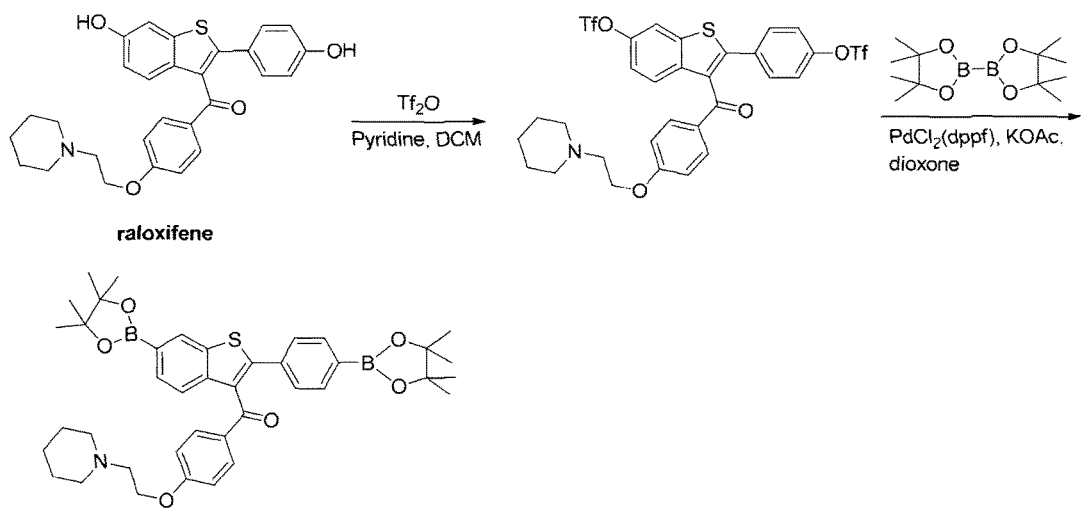
FIG. 7 shows the synthetic scheme for preparation of the pinacolyl boronate ester prodrug of raloxifene.
Figure 8:
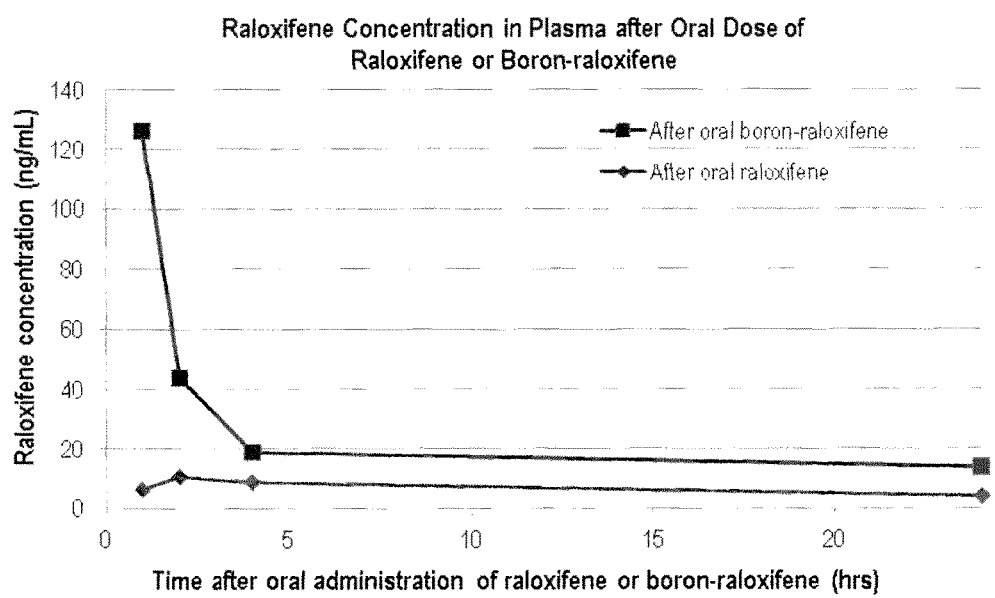
FIG. 8 shows the pharmacokinetic profile of boron-raloxifene in mouse plasma.

Pinacolyl Boronate Ester Prodrug of Raloxifene (FIGS. 7 & 8)

Step 1: A solution of trifluoromethanesulfonic anhydride (0.84 g, 0.48 mL, 3.0 mmol) in CH$_2$Cl$_2$ (5.0 mL) was added dropwise to a solution of pyridine (0.25 mL, 3.0 mmol) and raloxifene (0.47 g, 1 mmol) in anhydrous CH$_2$Cl$_2$ (10 mL) at 0° C. After complete addition, the mixture was warmed to room temperature and allowed to stir for 1 hour. The mixture was then diluted with Et$_2$O, quenched with 10% aq HCl and washed successively with sat. NaHCO$_3$ solution and brine. After drying over MgSO$_4$, the solvent was removed under reduced pressure and the residue was purified by flash column chromatography to give the ditriflates (0.16 g). $^1$H-NMR (300 MHz, CD$_3$Cl): 7.86-7.83 (m, 2H), 7.68 (d, J=8.4 Hz, 2H), 7.48 (d, J=8.4 Hz, 2H), 7.33 (dd, J=8.7 and 1.5 Hz, 1H), 7.16 (d, J=8.7 Hz, 2H), 6.77 (d, J=8.4 Hz, 2H), 4.34 (t, J=3.3 Hz, 2H), 3.36 (t, J=3.3 Hz, 2H), 3.10 (m, 4H), 1.92 (m, 4H), 1.62 (m, 2H). $^{13}$C-NMR (75 MHz, CD$_3$Cl): 191.4, 163.5, 149.7, 147.1, 144.8, 139.6, 139.1, 133.1, 132.6, 132.3, 131.0, 129.7, 125.4, 121.8, 118.7 (q, J=323 Hz), 115.1, 114.5, 66.1, 57.5, 55.0, 25.7, 24.0. HR-MS (ESI(+)): Calcd. for C$_{30}$H$_{26}$F$_6$NO$_8$S$_3$ (M+H): 738.0725. Found: 738.0721.

Step 2: To a 1,4-dioxane solution of the ditriflate (0.15 g, 0.20 mmol) were added bis(pinacolato)diboron (0.16 g, 0.60 mmol), PdCl$_2$(dppf) (0.030 g, 5% mol) and KOAc (0.14 g, 1.4 mmol), and the mixture was irradiated at 120° C. for 1 h under microwave. After the solution was cooled, the dioxane was removed under vacuum. The crude was purified by flash chromatography to afford product (87 mg). $^1$H-NMR (300 MHz, CD$_3$Cl): 8.14 (s, 1H), 7.84 (d, J=6.6 Hz, 2H), 7.63 (m, 2H), 7.45 (m, 2H), 7.32 (d, J=6.9 Hz, 2H), 6.81 (d, J=8.1 Hz, 2H), 6.70 (d, J=8.1 Hz, 2H), 5.16 (s, 2H), 4.22 (m, 2H), 3.13 (m, 4H), 2.31 (s, 3H), 1.84 (m, 4H), 1.66 (m, 4H), 1.26 (s, 24H). $^{13}$C-NMR (75 MHz, CD$_3$Cl): 156.8, 139.0, 137.5, 134.7, 131.5, 131.2, 129.8, 128.7, 128.3, 127.4, 126.8, 114.6, 110.4, 109.6, 83.5, 83.4, 83.1, 82.8, 80.3, 75.0, 69.7, 56.0, 55.3, 46.9, 26.8, 25.0, 24.9, 24.5, 24.1, 22.7, 9.5. HR-MS (ESI(+)): Calcd for C$_{42}$H$_{57}$B$_2$N$_2$O$_5$ (M+H): 691.4454. Found: 691.4460.

To determine if boron-raloxifene derivatives have enhanced bioavailability in vivo, mice were given 5 mg/kg each of raloxifene or boron-raloxifene as a single oral dose and plasma concentration of raloxifene was monitored in each group of mice. Raloxifene concentration in mouse plasma was significantly higher in the group given oral boron-raloxifen than that of mice administered with oral raloxifene (FIG. 8).

EXAMPLE 4

Figure 9:
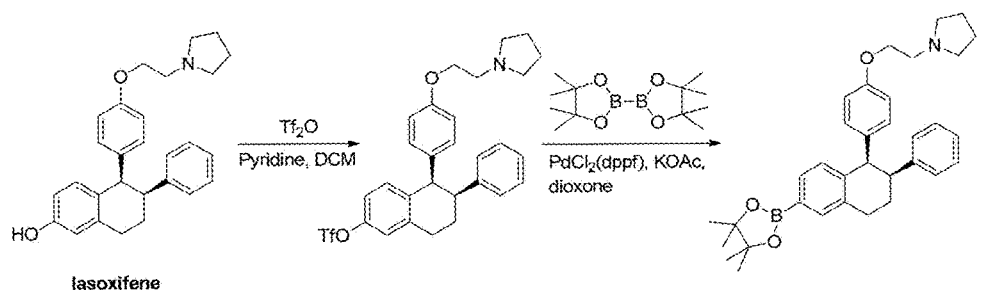
FIG. 9 shows the synthetic scheme for preparation of the pinacolyl boronate ester prodrug of lasofoxifene.
Figure 10:
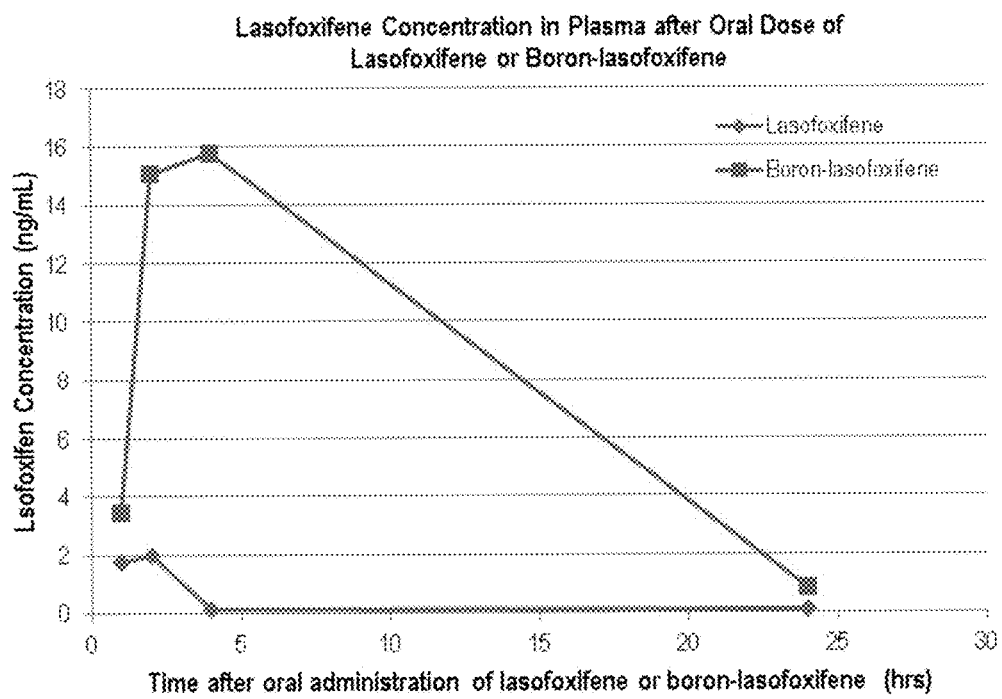
FIG. 10 shows the pharmacokinetic profile boron-lasofoxifene in mouse plasma.

Pinacolyl Boronate Ester Prodrug of Lasofoxifene (FIGS. 9 & 10)

Step 1: A solution of trifluoromethanesulfonic anhydride (0.84 g, 0.48 mL, 3.0 mmol) in CH$_2$Cl$_2$ (5.0 mL) was added dropwise to a solution of pyridine (0.25 mL, 3.0 mmol) and lasoxifene (0.41 g, 1 mmol) in anhydrous CH$_2$Cl$_2$ (10 mL) at 0° C. After complete addition, the mixture was warmed to room temperature and allowed to stir for 1 hour. The mixture was then diluted with Et$_2$O, quenched with 10% aq HCl and washed successively with sat. NaHCO$_3$ solution and brine. After drying over MgSO$_4$, the solvent was removed under reduced pressure and the residue was purified by flash column chromatography to give the triflates of lasoxifene (0.15 g).

Step 2: To a 1,4-dioxane solution of the triflate of lasoxifene (0.15 g, 0.27 mmol) were added bis(pinacolato)diboron (80 mg, 0.30 mmol), PdCl$_2$(dppf) (0.015 g, 5% mol) and KOAc (70 mg, 0.7 mmol), and the mixture was irradiated at 120° C. for 1 h under microwave irradiation. After the solution was cooled, the dioxane was removed under vacuum, the crude was purified by flash chromatography to afford product (0.13 g). $^1$H-NMR (300 MHz, CD$_3$Cl): 7.74 (s, 1H), 7.53 (d, J=7.2 Hz, 1H), 7.19-7.18 (m, 3H), 6.96 (d, J=7.2 Hz, 1H), 6.83 (m, 2H), 6.52 (d, J=7.8 Hz, 2H), 6.32 (d, J=8.4 Hz, 2H), 4.32-4.30 (m, 3H), 3.42-3.14 (m, 9H), 2.16-2.09 (m, 4H), 1.88 (m, 2H). $^{13}$C-NMR (75 MHz, CD$_3$Cl): 155.6, 143.9, 143.1, 136.0, 135.7, 135.5, 132.0, 131.7, 130.1, 128.1, 127.8, 126.1, 112.9, 64.0, 42.6, 54.2, 51.1, 45.0, 29.6, 24.9, 23.2. HR-MS (ESI(+)): Calcd for C$_{34}$H$_{43}$BNO$_3$ (M+H): 524.3336. Found: 524.3329.

To determine if boron-lasofoxifene derivatives have enhanced bioavailability in vivo, mice were given 5 mg/kg each of lasofoxifene or boron-lasofoxifene as a single oral dose and plasma concentration of lasofoxifene was monitored in each group of mice. The systemic bioavailability of lasofoxifene when boron-lasofoxifen was administered was much improved over that afforded by direct oral administration of lasofoxifene (FIG. 10).

EXAMPLE 5

Figure 11:
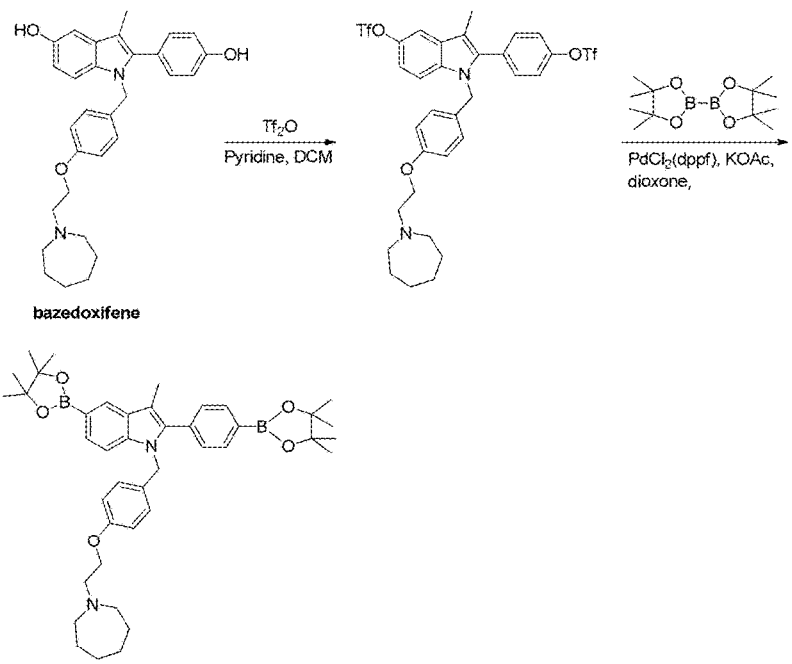
FIG. 11 shows the synthetic scheme for preparation of the pinacolyl boronate ester prodrug of bazedoxifene.

Pinacolyl Boronate Ester-Prodrug of Bazedoxifene (FIG. 11)

Step 1: A solution of trifluoromethanesulfonic anhydride (0.84 g, 0.48 mL, 3.0 mmol) in CH$_2$Cl$_2$ (5.0 mL) was added dropwise to a solution of pyridine (0.25 mL, 3.0 mmol) and bazedoxifene (0.47 g, 1 mmol) in anhydrous CH$_2$Cl$_2$ (10 mL) at 0° C. After complete addition, the mixture was warmed to room temperature and allowed to stir for 1 hour. The mixture was then diluted with Et$_2$O, quenched with 10% aq HCl and washed successively with sat. NaHCO$_3$ and brine. After drying over MgSO$_4$, the solvent was removed under reduced pressure and the residue was purified by flash column chromatography to give the ditriflates (0.87 g).

¹H-NMR (300 MHz, CD₃Cl): 7.50 (d, J=1.8 Hz, 1H), 7.36 (m, 4H), 7.20 (d, J=9.0 Hz, 1H), 7.08 (dd, J=8.7 and 2.1 Hz, 1H), 6.82-6.75 (m, 4H), 5.15 (s, 2H), 4.35 (t, J=3.9 Hz, 2H), 3.64-3.61 (m, 4H), 3.18 (m, 2H), 3.26 (s, 3H), 1.97 (m, 4H), 1.75 (m, 4H). ¹³C-NMR (75 MHz, CD₃Cl): 156.5, 149.4, 143.6, 137.9, 135.7, 132.2, 131.7, 130.9, 128.9, 127.5, 121.7, 120.2 (q, J=317 Hz), 118.9 (q, J=319 Hz), 118.8 (q, J=321 Hz), 115.6, 114.9, 111.7, 111.1, 111.0, 62.8, 56.7, 56.1, 47.3, 26.3, 23.5, 9.3. HR-MS (ESI(+)): Calcd. for $C_{32}H_{33}F_6N_2O_7S_2$ (M+H): 735.1633. Found: 735.1635.

Step 2: To a 1,4-dioxane solution of the ditriflate (0.15 g, 0.20 mmol) were added bis(pinacolato)diboron (0.16 g, 0.60 mmol), PdCl₂(dppf) (0.030 g, 5% mol) and KOAc (0.14 g, 1.4 mmol), and the mixture was irradiated at 120° C. for 1 h under microwave. After the solution was cooled, the dioxane was removed under vacuum. The crude was purified by flash chromatography to afford product (87 mg). ¹H-NMR (300 MHz, CD₃Cl). ¹³C-NMR (75 MHz, CD₃Cl). HR-MS (ESI(+)): Calcd for $C_{42}H_{57}B_2N_2O_5$ (M+H): 691.4454. Found: 691.4460.

EXAMPLE 6

Figure 12:
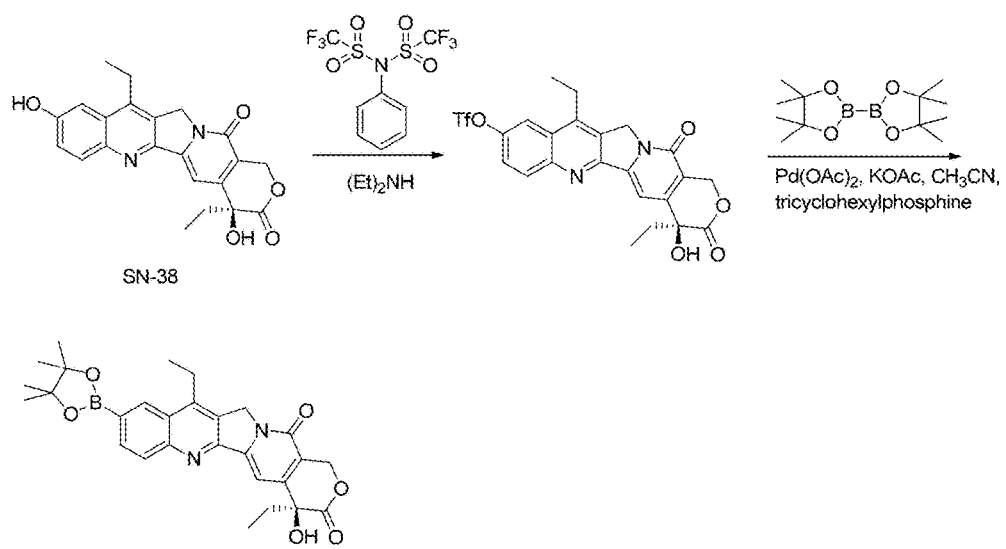
FIG. 12 shows the synthetic scheme for preparation of the pinacolyl boronate ester prodrug of SN-38.

Pinacolyl Boronate Ester Prodrug of SN-38 (FIG. 12)

Step 1: To the solution of SN-38 (1.2 g, 3.05 mmol) in DMF (30 mL), was added diethyl amine (0.85 mL, 6.12 mmol) and 1,1,1-trifluoro-N-phenyl-N-((trifluoromethyl)sulfonyl) methanesulfonamide (1.64 g, 4.58 mmol). The resultant mixture was stirred at 50° C. for 3 h. The reaction mixture was diluted with DCM and quenched with water. The organic layer was dried over Na₂SO₄ and concentrated. The crude was purified by flash column to afford solid the triflate product (2.1 g).

Step 2: The mixture of the triflate of SN-38 (1.7 g, 3.24 mmol), bis(pinacolato)diboron (1.2 g, 4.86 mmol), potassium acetate (0.875 g, 9.72 mmol), Pd(OAc)₂ (40 mg) and tricyclohexylphosphine (100 mg) in acetonitrile (60 mL) was stirred at 80° C. under N₂ for 4 h. The solvent was removed under vacuum and the crude was purified by flash chromatography to afford product (0.80 g). ¹H-NMR (CDCl₃, 300 MHz): 8.60 (s, 1H), 8.18-8.17 (m, 2H), 7.68 (s, 1H), 5.76 (d, J=16.2 Hz, 1H), 5.34-5.27 (m, 3H), 3.79 (s, 1H), 3.28 (m, 2H), 1.90 (m, 2H), 1.46-1.42 (m, 15H), 1.04 (t, J=7.5 Hz, 3H). ¹³C-NMR (CDCl₃, 75 MHz): 174.0, 157.7, 152.7, 151.0, 150.2, 147.1, 146.5, 135.0, 131.2, 129.7, 126.8, 126.3, 118.6, 98.2, 84.4, 72.8, 66.4, 49.5, 31.6, 24.9, 23.0, 14.4, 7.8. HR-MS (ESI(+)): Calcd. for $C_{28}H_{32}BN_2O_6$ (M+H): 503.2353. Found: 503.2357.

EXAMPLE 7

Figure 13:
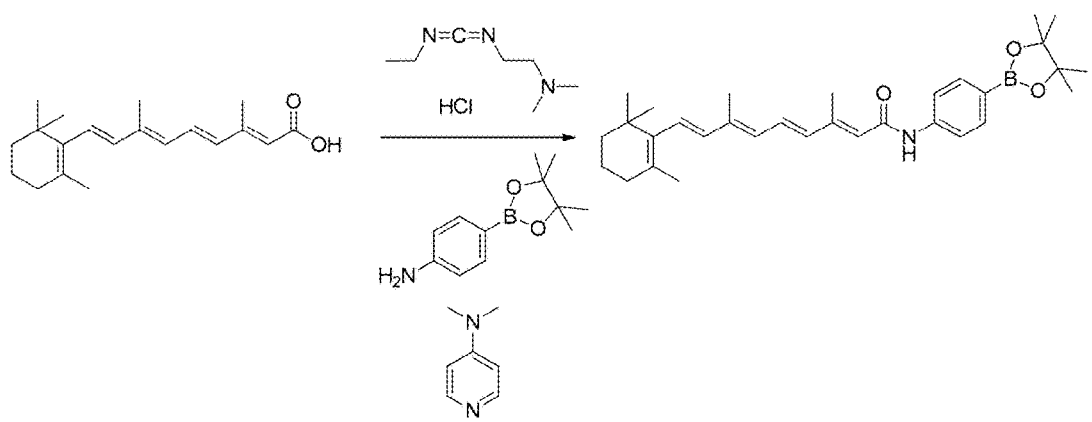
FIG. 13 shows the synthetic scheme for preparation of the pinacolyl boronate ester prodrug of fenretinide.

Pinacolyl Boronate Ester Prodrug of Fenretinide (FIG. 13)

The mixture of retinoic acid (0.5 g, 1.6 mmol), 4-(4,4,5,5-tetramethyl-1,3,2-dioxaborolan-2-yl)aniline (0.36 g, 1.6 mmol), EDCI (0.36 g, 2.0 mmol) and DMAP (0.2 g, 1.6 mmol) in 20 mL of dichloromethane was stirred at room temperature overnight until the reaction finish completely. The reaction mixture was applied to a silica gel column and eluted with an ethyl acetate/hexane to afford the product (0.12 g) as yellow oil that solidifies on standing. ¹H-NMR (CDCl₃, 300 MHz): 7.76 (d, J=7.2 Hz, 2H), 7.58 (d, J=7.2 Hz, 2H), 7.28 (m, 1H), 7.05-6.92 (m, 2H), 6.30-6.12 (m, 2H), 5.80 (s, 1H), 2.43-0.86 (m, 3314). ¹³C-NMR (CDCl₃, 75 MHz): 165.2, 151.2, 141.0, 139.4, 137.7, 137.3, 135.8, 135.2, 130.7, 130.0, 129.5, 128.6, 121.0, 118.4, 83.7, 39.6, 34.3, 33.1, 29.0, 24.9, 21.7, 19.2, 13.7, 12.9. MS (ESI(+)): 502.2 (M+).

EXAMPLE 8

Figure 14:
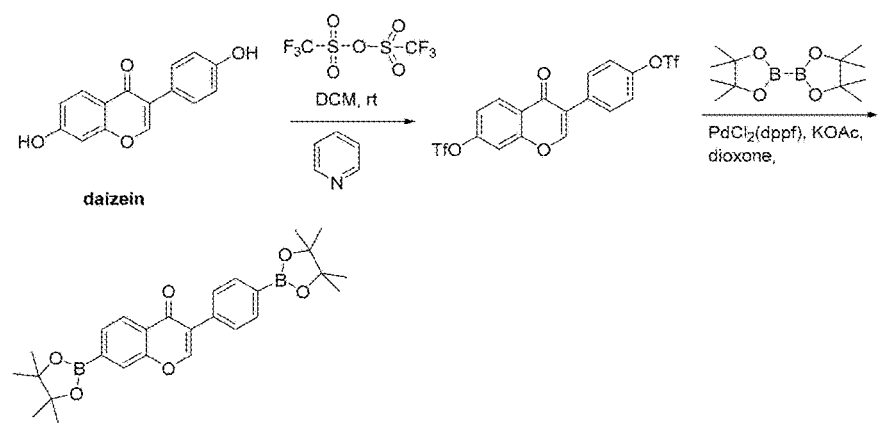
FIG. 14 shows the synthetic scheme for preparation of the pinacolyl boronate ester prodrug of daidzein.

Pinacolyl Boronate Ester Prodrug of Daizein (FIG. 14)

Step 1: Daidzein (1.27 g, 0.005 mol) was dissolved in DCM (30 mL), then trifluoromethanesulfonic acid anhydride (3.2 g, 0.011 mol, d 1.677, 1.86 mL) and 4-dimethylaminopyridine (1.22 g, 0.01 mol) were added and the resulting mixture was stirred until the reaction was finished. The reaction was quenched with satd. sodium carbonate solution and extracted with ethyl acetate. The combined organic layer was dried over MgSO₄ and concentrated. The crude was purified by flash column to afford solid product (0.40 g). ¹H-NMR (CDCl₃, 300 MHz): 8.43 (d, J=8.7 Hz, 1H), 8.08 (s, 1H), 7.66 (d, J=8.7 Hz, 2H), 7.50 (m, 1H), 7.42-7.33 (m, 3H). ¹³C-NMR (CDCl₃, 75 MHz): 174.5, 156.4, 153.7, 152.4, 149.6, 131.4, 130.8, 129.3, 124.5, 124.1, 121.7, 119.1, 118.8 (q, J=319 Hz), 111.6. GC-MS: 518.1 (M+).

Step 2: The triflate (0.26 g, 0.5 mmol), diboron reagent (0.36 g, 3.6 mmol), PdCl₂(dppf) (0.014 g, 0.16 mmol) and potassium acetate (0.24 g, 2.4 mmol) was dissolved in dioxane (3 mL), then the mixture was stirred at 80° C. under microwave irradiation. The solvent was removed under vacuum and the crude purified by flash chromatography to afford product (0.12 g). ¹H-NMR (CDCl₃, 300 MHz): 8.29 (d, J=7.8 Hz, 1H), 8.06 (s, 1H), 7.93-7.87 (m, 3H), 7.81 (d, J=7.8 Hz, 1H), 7.60 (d, J=7.8 Hz, 2H), 1.38 (s, 12H), 1.36 (s, 12H). ¹³C-NMR (CDCl₃, 75 MHz): 176.2, 155.6, 153.5, 134.9, 134.8, 130.7, 128.2, 126.3, 125.5, 125.4, 124.5, 84.6, 83.9, 24.90, 24.88. GC-MS: 474.3 (M+). HRMS (ESI(+)): Calcd. for $C_{15}H_{13}B_2O_6$ (diboronic acid) (M+H): 311.0898. Found: 311.0897.

EXAMPLE 9

Figure 15:
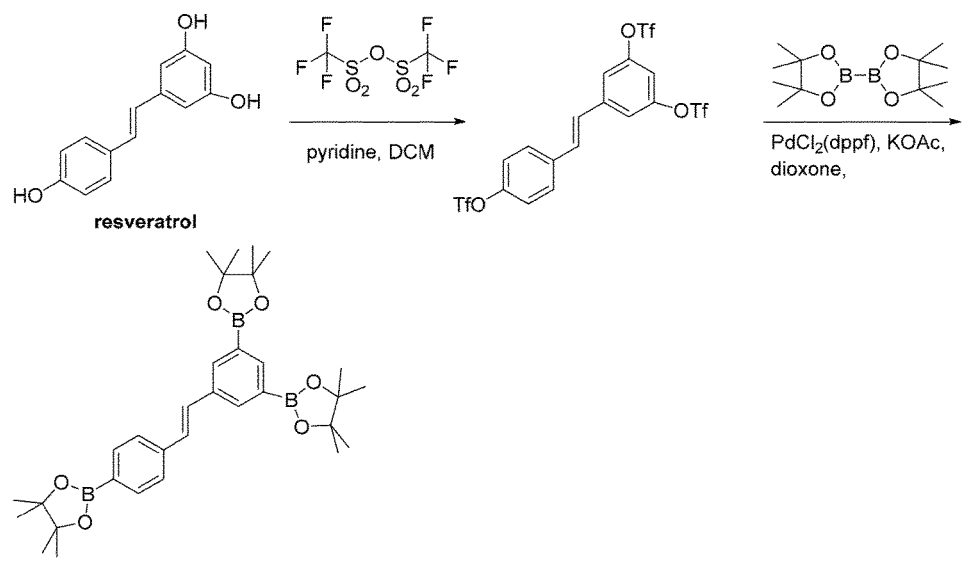
FIG. 15 shows the synthetic scheme for preparation of the pinacolyl boronate ester prodrug of resveratrol.

Pinacolyl Boronate Ester Prodrug of Resveratrol (FIG. 15)

Step 1: A solution of trifluoromethanesulfonic anhydride (d 1.487, 3.7 mL, 19.5 mmol) in CH₂Cl₂ (5.0 mL) was added dropwise to a solution of pyridine (d, 0.9819, 1.96 mL, 24.3 mmol) and the corresponding phenol (1.2 g, 5.3 mmol) in anhydrous CH₂Cl₂ (10 mL) at 0° C. After complete addition, the mixture was warmed to room temperature and allowed to stir overnight. The mixture was then diluted with ethyl acetate, quenched with brine. The organic layer was separated. The aqueous solution was extracted with ethyl acetate. The combined organic solution was dried over MgSO₄. After drying, the solvent was removed under reduced pressure and the residue was purified by flash column chromatography to give the triflates (3.3 g) quantatively. ¹H-NMR (CDCl₃, 300 MHz): 7.63 (d, J=8.7 Hz, 2H), 7.46 (d, J=1.5 Hz, 2H), 7.33 (d, J=8.4 Hz, 2H), 7.21-7.04 (m, 3H). ¹³C-NMR (CDCl₃, 75 MHz): 149.8, 149.6, 141.3, 136.0, 131.6, 128.7, 126.7, 122.0, 119.3, 118.8 (q, J=319 Hz), 118.7 (q, J=319 Hz), 114.1.

Step 2: The resveratrol triflates (1.24 g, 2 mmol), bis(pinacolato)diboron (1.66 g, 6.6 mmol), PdCl₂(dppf) (0.14 g, 2.5 mol %) and KOAc (0.88 g, 9 mmol) in dioxane (5 mL) were stirred at 120° C. under nitrogen for 2 h. TLC and MS showed that the triflate was consumed completely and there is product to form. The solvent was removed under vacuum and the crude purified by flash chromatography to afford product (0.86 g). ¹H-NMR (CDCl₃, 300 MHz): 8.19 (s, 1H), 8.07 (s, 2H), 7.81 (d, J=8.1 Hz, 2H), 7.52 (d, J=7.8 Hz, 2H), 7.23 (s, 2H), 1.37 (s, 12), 1.28 (s, 24H). $^{13}$C-NMR (CDCl$_3$, 75 MHz): 140.6, 140.2, 135.8, 135.1, 129.5, 128.6, 125.7, 83.9, 83.5, 25.0, 24.9. HRMS (ESI(+)): Calcd. for C$_{14}$H$_{18}$B$_3$O$_6$ (triboronic acid) (M+H): 313.1226. Found: 313.1228.

EXAMPLE 10

Figure 16:
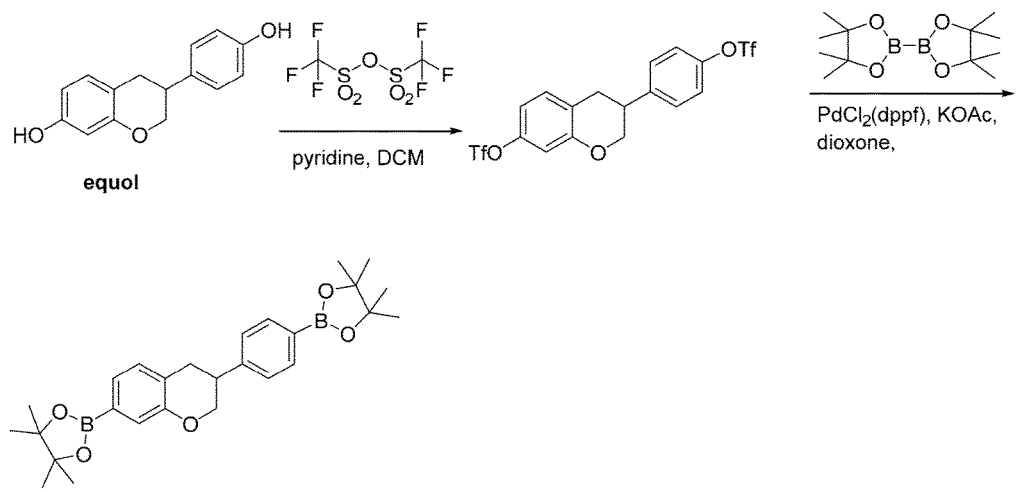
FIG. 16 shows the synthetic scheme for preparation of the pinacolyl boronate ester prodrug of equol.

Pinacolyl Boronate Ester Prodrug of Equol (FIG. 16)

Step 1: Equol (1.22 g, 0.005 mol) was dissolved in DCM (30 mL), then trifluoromethanesulfonic acid anhydride (1.6 g, 0.0055 mol, d 1.677, 0.93 mL) and 4-dimethylaminopyridine (0.61 g, 0.005 mol) were added and the resulting mixture was stirred until the reaction was finished. The reaction was quenched with satd. sodium carbonate solution and extracted with ethyl acetate. The combined organic layer was dried over MgSO$_4$ and concentrated. The crude was purified by flash column to afford solid product (1.71 g). $^1$H-NMR (CDCl$_3$, 300 MHz): 7.35-7.22 (m, 4H), 7.15 (d, J=9.0 Hz, 1H), 6.83-6.81 (m, 2H), 4.33 (m, 1H), 4.06 (m, 1H), 3.29 (m, 1H), 3.06-3.03 (m, 2H). $^{13}$C-NMR (CDCl$_3$, 75 MHz): 155.0, 148.7, 148.5, 141.1, 130.8, 129.2, 121.9, 121.8, 118.7 (q, J=318 Hz), 113.4, 109.9, 70.4, 37.5, 31.8. GC-MS: 506.1 (M+).

Step 2: The triflate (0.51 g, 1.0 mmol), bis(pinacolato)diboron (0.63 g, 2.5 mmol), PdCl$_2$(dppf) (0.014 g, 0.16 mmol) and potassium acetate (0.24 g, 2.4 mmol) was dissolved in dioxane (3 mL), then the mixture was stirred at 80° C. under microwave irradiation. The solvent was removed under vacuum and the crude purified by flash chromatography to afford product (0.10 g). $^1$H-NMR (CDCl$_3$, 300 MHz): 7.80 (d, J=7.8 Hz, 2H), 7.31-7.27 (m, 4H), 7.10 (d, J=7.5 Hz, 1H), 6.83-6.81 (m, 2H), 4.33 (m, 1H), 4.02 (t, J=10.2 Hz, 1H), 3.25 (m, 1H), 3.08-3.03 (m, 2H), 1.34 (s, 24H). $^{13}$C-NMR (CDCl$_3$, 75 MHz): 154.0, 144.6, 135.3, 129.3, 126.8, 126.5, 125.2, 122.8, 83.8, 83.7, 70.7, 38.8, 32.5, 24.8. GC-MS: 462.4 (M+). HRMS (ESI(+)): Calcd. for C$_{15}$H$_{17}$B$_2$O$_5$ (diboronic acid) (M+H): 299.1262. Found: 299.1268.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A compound of Formula 29:

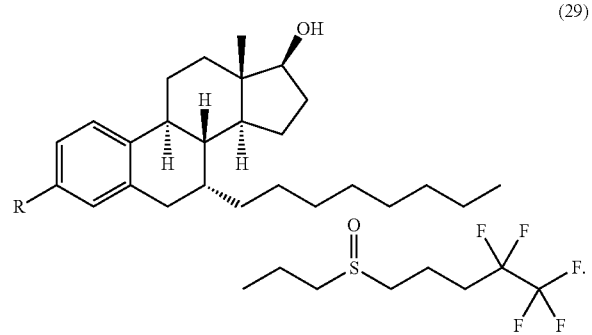

wherein R is selected from the group consisting of:

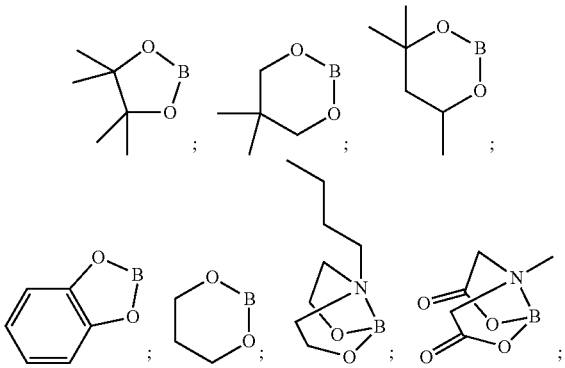

KF$_{3B}$; (HO)$_2$B; and NaF$_3$B; and
wherein the boron atom is the point of attachment in each R variable substituent, and any salts thereof.

2. The compound of claim 1, wherein R is

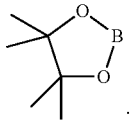

3. The compound of claim 1, wherein R is: (HO)$_2$B.

4. A pharmaceutical composition comprising the compound of claim 1.

5. A method of treating breast cancer in a mammal in need thereof, the method comprising administering to said mammal the compound of claim 1 in an amount that is therapeutically effective for said treatment.

6. A method of downregulating an estrogen receptor in a mammal in need thereof, the method comprising administering to said mammal the compound of claim 1 in an amount that is therapeutically effective for said downregulation.

* * * * *